United States Patent [19]

van Andel

[11] Patent Number: Plant 6,784

[45] Date of Patent: May 9, 1989

[54] ALSTROEMERIA VARIETY 'STALVIR'

[75] Inventor: Jacob van Andel, Aalsmeer, Netherlands

[73] Assignee: Van Staaveren, B.V., Aalsmeer, Netherlands

[21] Appl. No.: 23,761

[22] Filed: Mar. 9, 1987

[51] Int. Cl.[4] ..... A01H 5/00
[52] U.S. Cl. ..... Plt./68
[58] Field of Search ..... Plt./68

*Primary Examiner*—Robert E. Bagwill
*Attorney, Agent, or Firm*—Charles W. Rummler

[57] ABSTRACT

A new variety of Alstroemeria characterized by its relatively small blooms, having a generally overall pink coloration for both its inner and outer petals, the inner petals having short, parallel streaks of a purplish color which extends from the petal base to the tip in a longitudinal manner, the inner petals being more narrow in form and being mainly of the principal pink color with the larger two having a yellowish flush over the base portion of the petals. Each of both the inner and outer petals have a darker pink flush over the central portion of the petal body and at the petal tips.

The flowers grow in a rather umbel-like, closely-spaced formation at the ends of straight stems thereby presenting a very attractive, closely spaced grouping of the flower, particularly suited for vase keeping. This new variety of alstroemeria is further distinguished by its strong, vigorous and upright growth habit with the main stems reaching a height up to about 160 cm. and each stem bearing a group of many flowers at its upper end and the plant flowering continuously throughout the year to provide an excellent production habit.

1 Drawing Sheet

BACKGROUND OF THE NEW PLANT

This new Alstroemeria plant was a selected seedling from a group grown at Aalsmeer, The Netherlands, from a hybrid resulting from my crossing the variety 'Edison' as the seed parent with a stock variety identified by the number 7258-3 as the pollen parent. The pollen parent was selected from my breeding stock maintained at Aalsmeer, and this crossing having been done with the object of developing a plant having better production of blooming stems and new color for the blooms. This new plant was asexually reproduced under my direction by root division and the resulting plants showed the novel and desirable characteristics of the parent seedling. Further propagation was carried on under my direction at Aalsmeer through several succeeding generations by root stock division, which demonstrated that the novel and distinctive characteristics of the selected seedling would hold true from generation to generation and appeared to be firmly fixed for continual asexual propagation.

DESCRIPTION OF THE DRAWING

This new Alstroemeria hybrid is illustrated by the accompanying photographic drawing which, shows a group of flowers of a plant in full bloom one of which has been painted to demonstrate the unique and distinctive coloration and form of the flower.

DESCRIPTION OF THE NEW PLANT

The following is a detailed description of my new alstroemeria hybrid as observed at Aalsmeer, The Netherlands, with color designations being according to The R.H.S. Colour Chart published in 1966 by The Royal Horticultural Society of London, England.

THE PLANT

Origin: Seedling.
Parentage:

*Seed parent.*—The variety 'Edison' (unpatented).
*Pollen parent.*—Breeding Stock Plant No. 7258-3 maintained in my collection at Aalsmeer for breeding purposes.
Classification: Alstroemeria hybrid.
Form: Erect and tall bush.
Height: Up to about 160 cm. depending on growth rate from the bulb eyelets.
Flower stems:
*Length.*—About 15 cm. in simple umbel arrangement at the top of the main stem.
Growth: Vigorous, strong and upright.
Foliage:
*Quantity.*—Abundant.
*Number of leaves.*—About 30 to 40 leaves on the principal main stem.
*Size of leaf.*—Depending on season.
*Shape.*—Elliptic with entire margins.
*Texture.*—Leathery.
*Color.*—Upper side — Dark Green. Under side — Middle Green/Gray.
Rhizomes:
*Color.*—White.
*Size.*—Varying with the age of the plant.

THE BUD

Form: Pear shaped.
Size: Medium.
*Diameter.*—About 1.5 cm.
*Length.*—About 3 cm.
Calyx: This plant has no calyx, the six petals of the flower being perianth and dividing simultaneously.
Peduncle:
*Length.*—About 1.5 cm.
*Color.*—Middle green.

THE FLOWER

Blooming habit: Continuous throughout the year.
Flower size: Small.
*Diameter.*—About 4.5 cm.

*Depth.*—About 4 cm.

Borne: Singly on pedicels of a compound umbel.

Shape: Funnel-like with petal tips curling outwardly.

Petalage:

*Number of petals.*—Six.

*Arrangement.*—Two concentric groups with three petals in each group, the larger outer petals being spaced apart about 120 degrees and the smaller inner petals being in a generally 'Y' formation of which each of the two upper petals are spaced at least 160 degrees from the lower petal with their lower ends or base portions overlapping.

*Form.*—Outer petals, obovate and emarginate with entire margins.

*Texture.*—Leathery.

*Appearance.*—Shiny.

*Color.*—Outer petal: Top side — Generally Pink, 55A. Reverse side — Much lighter, 55C. Inside petal: Generally 55C with middle to base portion 12C, the entire surface of the inner petals being marked with numerous short, pencil stripes extending longitudinally. Reverse side: The same as the top side.

Persistence: The flowers hang on and dry.

Lasting quality:

*On plant.*—About 15 days.

*As a cut flower.*—About 10 days.

REPRODUCTIVE ORGANS

Stamens:

*Number.*—Six.

*Arrangement.*—Normal, one opposite each petal.

*Anthers.*—Color: Gray/Violet.

*Filaments.*—Length: About 4 cm. Color: Violet.

*Pollen.*—Color: Yellow/Green.

Pistil:

*Number.*—One.

*Style.*—Length: Varies with age. Color: Violet.

*Stigma.*—Color: Violet.

I claim:

1. A new and distinctive Alstroemeria hybrid and the parts thereof, substantially as herein shown and described, characterized by its small, closely grouped blossoms of a generally pink coloration, each of the inner petals having a yellow coloration from the middle of the petal body to the base and the entire petal surface being marked with many short pencil stripes spreading longitudinally from the petal base into all margins and to its tip.

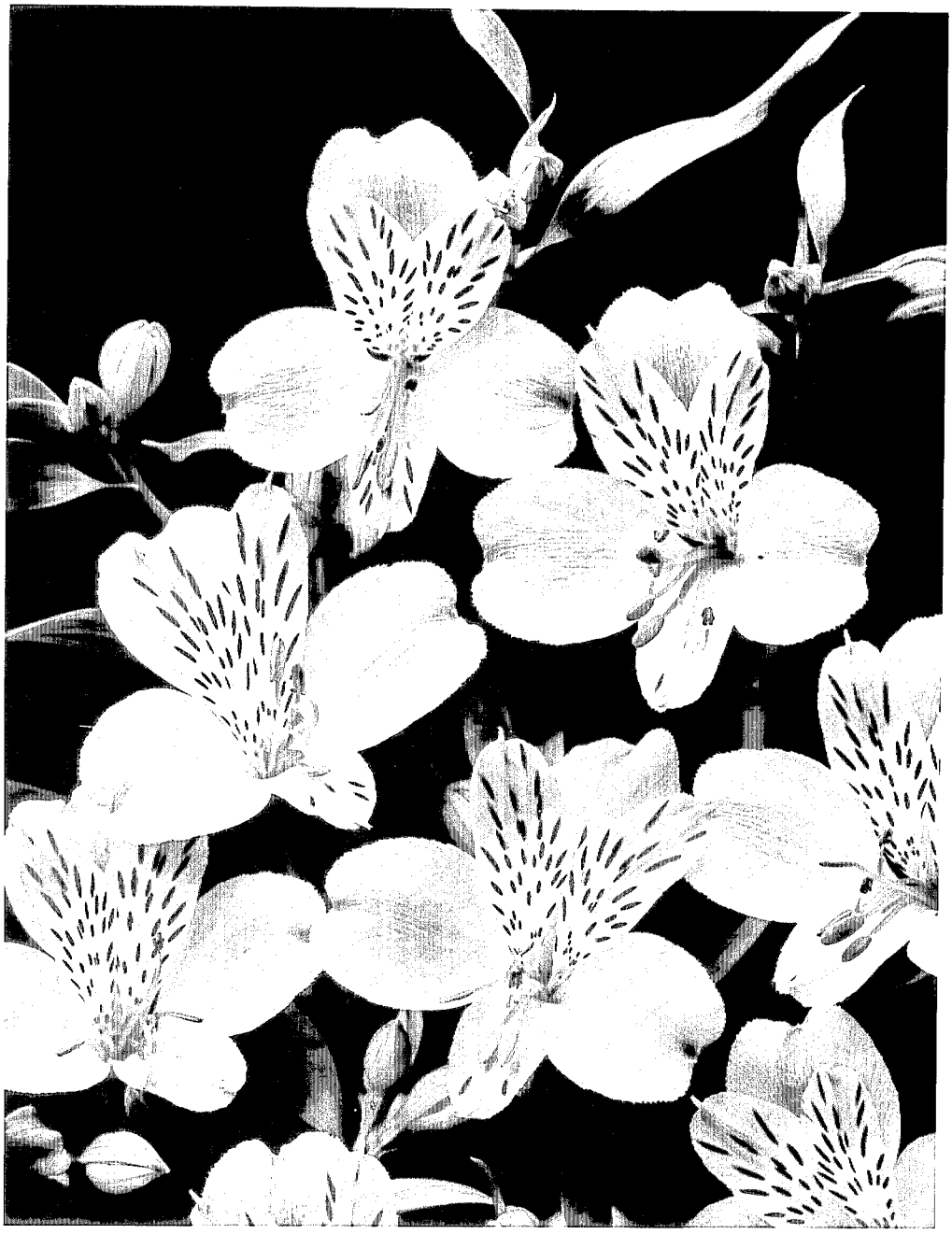

* * * * *